US011666717B2

(12) United States Patent
Boulanger et al.

(10) Patent No.: US 11,666,717 B2
(45) Date of Patent: Jun. 6, 2023

(54) RESUSCITATION BAG SYSTEM WITH A GAS CONTROL UNIT

(71) Applicants: L'Air Liquide, Société Anonyme pour l'Etude et l'Exploitation des Procédés Georges Claude, Paris (FR); Air Liquide Medical Systems, Antony (FR)

(72) Inventors: Thierry Boulanger, Philadelphia, PA (US); Jean-Christophe Richard, Sevrier (FR)

(73) Assignees: Air Liquide Medical Systems, Antony (FR); L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 452 days.

(21) Appl. No.: 16/880,012

(22) Filed: May 21, 2020

(65) Prior Publication Data

US 2020/0368470 A1 Nov. 26, 2020

(30) Foreign Application Priority Data

May 23, 2019 (EP) .................................. 19176115

(51) Int. Cl.
*A61M 16/00* (2006.01)
*A61M 16/20* (2006.01)
(Continued)

(52) U.S. Cl.
CPC .... *A61M 16/0084* (2014.02); *A61M 16/0078* (2013.01); *A61M 16/024* (2017.08);
(Continued)

(58) Field of Classification Search
CPC .............. A61M 16/00; A61M 16/0045; A61M 16/0057; A61M 16/0075; A61M 16/0078;
(Continued)

(56) References Cited

U.S. PATENT DOCUMENTS 4,362,153 A 12/1982 Wilson et al.
4,686,974 A * 8/1987 Sato .................... A61M 16/024
128/207.18

(Continued)

FOREIGN PATENT DOCUMENTS

DE 92 08 860 10/1992
GB 1 498 059 1/1978
(Continued)

OTHER PUBLICATIONS

International Search Report and Written Opinion for corresponding EP 19 17 6115, dated Nov. 28, 2019.

*Primary Examiner* — Joseph D. Boecker
(74) *Attorney, Agent, or Firm* — Allen E. White

(57) ABSTRACT

A resuscitation bag system (1) useable for resuscitating a person in cardiac arrest, and having a gas control unit (90) with a first valve (92) fluidly connected to a first (922) and to a second conduit (923), the first (922) and second conduits (923) being arranged in parallel and further fluidly connected to the first conduit element (56), the first conduit (922) having a first flow restriction (924) configured for limiting the gas flow to a first flowrate, and the second conduit (923) comprising second flow restriction (925) configured for limiting the gas flow to a second flowrate, with the second flowrate being less than the first flowrate.

14 Claims, 8 Drawing Sheets

(51) Int. Cl.
*A61M 16/10* (2006.01)
*A61M 16/08* (2006.01)

(52) U.S. Cl.
CPC ...... *A61M 16/1005* (2014.02); *A61M 16/202* (2014.02); *A61M 16/208* (2013.01); *A61M 16/0816* (2013.01); *A61M 2016/1025* (2013.01); *A61M 2202/0208* (2013.01); *A61M 2205/3306* (2013.01); *A61M 2205/3334* (2013.01); *A61M 2205/587* (2013.01)

(58) Field of Classification Search
CPC ............ A61M 16/0084; A61M 16/022; A61M 16/024; A61M 16/0816; A61M 16/0875; A61M 16/125; A61M 16/201; A61M 16/202; A61M 16/203; A61M 16/208; A61M 2016/003; A61M 2016/1005; A61M 2016/1025; A61M 2205/3306; A61M 2205/3334
See application file for complete search history.

(56) References Cited

U.S. PATENT DOCUMENTS

| | | | | |
|---|---|---|---|---|
| 5,735,268 | A | * | 4/1998 | Chua ................. A61M 16/024 128/207.14 |
| 5,964,220 | A | * | 10/1999 | Boussignac ........... A61M 16/00 128/200.24 |
| 2006/0060199 | A1 | * | 3/2006 | Lampotang ........... A61M 16/12 128/202.28 |
| 2012/0266879 | A1 | * | 10/2012 | Montgomery ........ A61M 16/20 128/203.14 |
| 2014/0261415 | A1 | * | 9/2014 | Acker ................ A61M 16/202 128/203.14 |
| 2019/0083724 | A1 | | 3/2019 | Boulanger |

FOREIGN PATENT DOCUMENTS

| | | |
|---|---|---|
| WO | WO 03 000328 | 1/2003 |
| WO | WO 2019 001751 | 1/2019 |
| WO | WO 2019 001752 | 1/2019 |

* cited by examiner

RESUSCITATION BAG SYSTEM WITH A GAS CONTROL UNIT

CROSS REFERENCE TO RELATED APPLICATIONS

This application claims the benefit of priority under 35 U.S.C. § 119 (a) and (b) to European Patent Application No. 19176115, filed May 23, 2019, the entire contents of which are incorporated herein by reference.

BACKGROUND

The present invention relates to an artificial respiration device, namely a resuscitation bag system with extended delivery capability that can be used for resuscitating a person, i.e. a patient, in state of cardiac arrest.

For treating a person in cardiac arrest, it is usual to operate a cardiac massage comprising thoracic compressions or 'TCs' along with intervals of lung ventilation with a resuscitation bag system.

TCs comprise successive compressions, manually operated by a rescuer, on the thoracic cage of the person, i.e. the patient, in cardiac arrest so that its thoracic cage goes "down" and $CO_2$-containing gases are expelled out of the lungs.

Two successive TCs are separated by a decompression or release phase, during which the rescuer stops exerting a manual pressure on the thorax of the patient so that the thoracic cage can goes "up" again, and fresh $O_2$-containing gases, such as air, oxygen-enriched air or pure oxygen, can enter into the lungs of the patient.

TCs aim at partially restoring inspiration and expiration phases and therefore gas exchange in the lungs, as well as promoting or restoring blood circulation toward and in the brain of the patient for avoiding or limiting cerebral hypoxia/anoxia.

As the successive compression/decompression phases only mobilize small volumes of gas in and out of the patient's airways, it is advocated to regularly perform additional gas insufflations to bring an oxygen-containing gas to the lungs, thereby enhancing the gas exchanges, especially the removal of $CO_2$ from the blood and the entering of $O_2$.

Fresh $O_2$-containing gas can be delivered to the patient by means of a resuscitation bag system associated to an oxygen source, such as a gas cylinder containing medical-grade $O_2$, that is fluidly connected to the patient via a respiratory interface, typically a facial mask, a laryngeal mask or an endotracheal tube. The flow of oxygen is usually set at about 15 L/min so that an oxygen concentration of about 100% V/V is reached upon insufflations, WO-A-2019/001751 and WO-A-2019/001752 teach examples of resuscitation bag systems useable during thoracic compressions.

Generally speaking, it is advocated to operate an insufflation of gas about every 15 TCs, for an ideal rate of compressions of between 100 and 120 compressions per minute (c/min), i.e. about 8 to 10 insufflations per minute. For practical reasons, the size and weight of an oxygen source, typically an oxygen cylinder, is limited so that a first rescuer can carry the oxygen cylinder to the place of emergency. For instance, D cylinders holding 425 L of oxygen and having a maximum weight of 4 kg (full) are commonly used. When the flow of oxygen gas is set at 15 L/min, such cylinders provide an autonomy of less than 30 min, which is often not sufficient as a cardiac massage may last up to 1 hour, or even more. In other words, there exists an antagonism between autonomy and maximum load/weight of gas cylinders used in cardiac resuscitation.

One goal of the present invention is hence to provide an improved resuscitation bag system dramatically decreasing the oxygen consumption, i.e. the quantity of oxygen needed, thereby ensuring an oxygen concentration of 100% v/v during a cardiac massage, i.e. during a cardiac resuscitation of a person in cardiac arrest, even for long periods of time, typically more than 30 min, preferably up to 1 hour, or even more, and further extending the autonomy of an oxygen cylinder without increasing its weight/size.

SUMMARY

A solution according to the present invention concerns a resuscitation bag system useable for resuscitating, i.e. for insufflating, a person in a state of cardiac arrest, comprising:
  a hollow flexible bag comprising an inlet and an outlet,
  a first conduct element fluidly connected to the inlet of the hollow flexible bag for providing gas to said flexible bag, and
  a main conduct fluidly connected to the outlet of the hollow flexible bag for conveying gas provided by said flexible bag,
characterized in that the resuscitation bag system further comprises a gas control unit comprising a first valve fluidly connected to a first and to a second conduct, said first and second conducts being arranged in parallel and further fluidly connected to the first conduct element, the first conduct comprising first flow restriction means configured for limiting the gas flow to a first flow rate, and the second conduct comprising second flow restriction means configured for limiting the gas flow to a second flow rate, said second flow rate being less than the first flow rate.

Depending on the embodiment, a resuscitation bag system according to the present invention can also comprise one or several of the following features:
  the first valve of the gas control unit is controlled by a monitoring module for directing the gas into the first conduct or the second conduct.
  the first and second conducts are fluidly connected to the first conduct element by means of a common line.
  the first flow restriction means comprise a first calibrated orifice for limiting the gas flow to a first flow rate.
  the second flow restriction means comprise a second calibrated orifice for limiting the gas flow to a second flow rate.
  the monitoring module comprises a processing means.
  the monitoring module further comprises a light emitter/receiver, preferably a light emitting diode as a light emitter and an avalanche photodiode as a light receiver.
  the resuscitation bag system further comprises a valve element arranged in the main conduct and comprising a venting port, and a main one-way valve arranged in the main conduct, between the hollow flexible bag and the valve element.
  the resuscitation bag system further comprises a derivation line fluidly connected to the main conduct, between the hollow flexible bag and the main one-way valve, and further to the valve element for controlling the opening or closing of said valve element.
  the first calibrated orifice is configured for limiting the gas flow to a first flow rate greater than 10 L/min, preferably a first flow rate of about 15 L/min.
  the second calibrated orifice is configured for limiting the gas flow to a second flow rate less than 2 L/min, preferably a second flow rate of about 0.5 L/min.

the monitoring module is fixed to the valve element.

the processing means comprise an electronic board comprising a control unit for processing data.

the control unit comprises a microprocessor, such as a microcontroller.

The invention also concerns a gas delivery assembly comprising:

a resuscitation bag system according to the invention, and a source of oxygen fluidly connected to the first valve of the resuscitation bag system via an oxygen line.

Preferably, the source of oxygen comprises an oxygen gas cylinder or the like.

The invention also concerns the use of a resuscitation bag system according to the invention or of a gas delivery assembly according to the invention for resuscitating a person, i.e. a patient, in a state of cardiac arrest, in particular for providing oxygen gas to said patient undergoing a cardiac massage by one or several rescuers, such as medical staff, comprising thoracic compressions (TCs) and intermittent lung ventilation.

BRIEF DESCRIPTION OF THE DRAWINGS

The present invention will be explained in more detail in the following illustrative description of an embodiment of a resuscitation bag system useable for insufflating a person in a state of cardiac arrest, in the frame of a resuscitation provided by a rescuer, which is made in reference to the accompanying drawings among them.

DETAILED DESCRIPTION OF THE PREFERRED EMBODIMENTS

Figure 1:
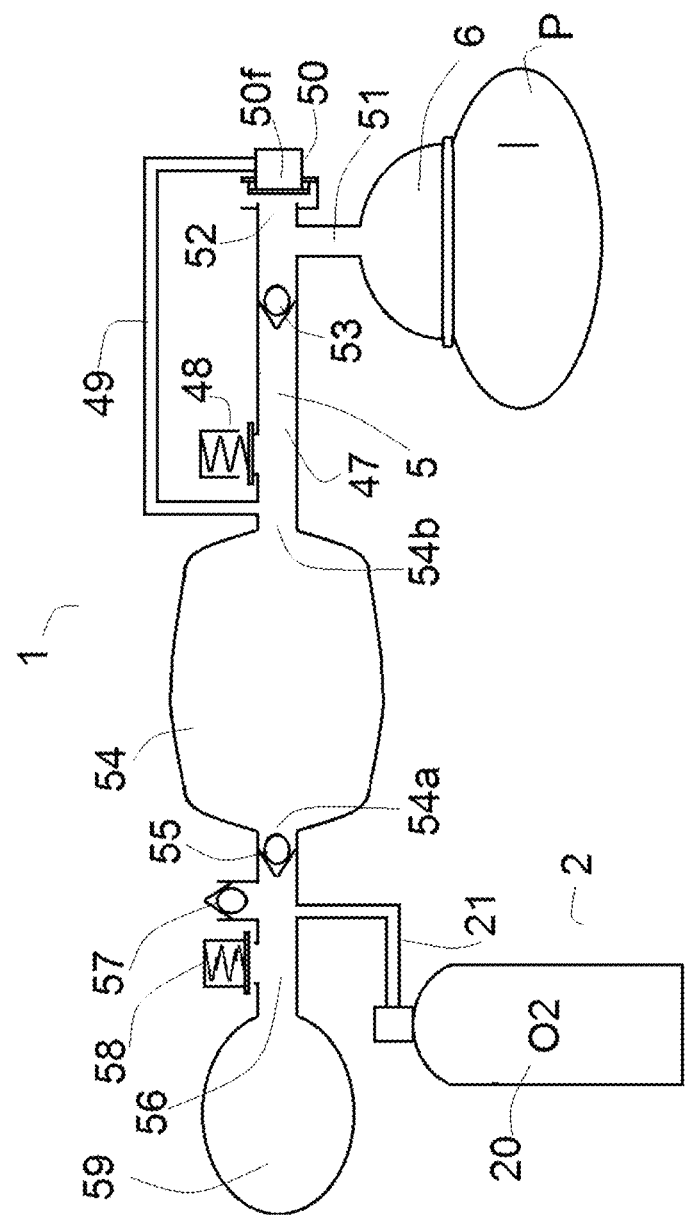
FIG. 1 shows a resuscitation bag system according to the prior art.

FIG. 1 shows an embodiment of a resuscitation bag system 1 of the prior art, such as disclosed by WO-A-2019/001751 or WO-A-2019/001752, for resuscitating a patient P in cardiac arrest, comprising a hollow flexible bag 54, i.e. a deformable enclosure, comprising an inlet 54a and an outlet 54b, i.e. orifices or the like.

The resuscitation bag system 1 comprises first conduct element 56 that is fluidly connected to the inlet 54a of the hollow flexible bag 54, i.e. upstream of the bag 54, for providing gas to said flexible bag 54, and further a main conduct 5 that is fluidly connected to the outlet 54b of the hollow flexible bag 54, i.e. downstream of the bag 54, for recovering and conveying gas provided by said flexible bag 54.

A valve element 50, also called control valve, arranged in the gas circuit, namely in the main conduct 5, downstream of the hollow flexible bag 54 for diverting the gas in and out of the patient P, during insufflation and exsufflation phases.

An oxygen source 2 comprising an $O_2$ cylinder 20 containing oxygen or an oxygen-containing gas provides oxygen or an oxygen-containing gas to the resuscitation bag system 1. Gas delivered by oxygen source 2 is conveyed by an oxygen line 21, i.e. gas conduct, hose or the like, that is fluidly connected, on the one hand, to the oxygen source 2 and, on the second hand, to the first conduct element 56 of resuscitation bag system 1, i.e. upstream of the flexible bag 54, for providing oxygen gas to the inlet 54a of the flexible bag 54.

A respiratory interface 6 is used for delivering respiratory gas to the patient P, typically a respiratory mask or the like, that is fed by the main conduct 5.

When the flexible bag 54 is squeezed by a rescuer, the $O_2$-containing gas contained in the flexible bag 54 flows out of the flexible bag 54 and is subsequently conveyed to the respiratory interface 6, via the main conduct 5 that comprises two successive portions or tubing elements, such as a first 47 and a second 51 portion or tubing element, fluidly connected together, such as gas conducts or the like. Main conduct 5 ensures a fluidic communication between flexible bag 54 and the respiratory interface 6 thereby allowing gas to travel from the flexible bag 54 to the respiratory interface 6.

A main one-way valve 53 arranged in the main conduct 5, namely in the first tubing element 47, controls the gaseous flow travelling in the lumen of tubing element 47 so that the gas can only travel in one way, namely from flexible bag 54 to interface 6, but not in the other way.

Valve element 50 is fluid connected to the main conduct 5, downstream of main one-way valve 53, preferably via a third portion or tubing element 52 that is in fluid communication to the first and second tubing elements 47, 51, i.e. they form a "T" junction or the like.

Valve element 50 comprises a venting port, also called exhaust port, fluidly communicating with the atmosphere for venting gas over-pressures in the main conduct 5 to the atmosphere, especially for controlling the pressure level in the second tubing element 51, for instance when the patient P expires gases, i.e. during exhalation phases, that are recovered into the second tubing element 51.

Further, a derivation line 49, i.e. a conduct or the like, is arranged between the first tubing element 47 and valve element 50 for controlling the opening or closing of valve element 50, and the venting of gas to the atmosphere. Actually, pressure provided by derivation line 49 exerts a pneumatic force that applies on a membrane or the like of valve element 50 that is arranged so as to open or close the venting port of valve element 50 thereby allowing or prohibiting gas to be vented to the atmosphere.

Such a resuscitation bag 1 system allows performing gas insufflations to the patient, while said patient is submitted to thoracic compressions (TCs) operated by another rescuer. Continuous TCs are made possible by controlling valve element 50 which opens whenever a pressure gradient existing between the second tubing element 51 and the derivation conduct 49 exceeds a given opening pressure, i.e. a given pressure threshold.

During a TC, the resuscitation bag system 1 is at rest, e.g., not squeezed by a rescuer. The positive pressure that is generated by a TC, closes the main one-way valve 53 and the gaseous flow coming out of the lungs of the patient P and recovered into interface 6, further travels successively in the lumen of the second and third tubing elements 51, 52, i.e. gas conducts, passages or the like, and is afterwards vented to the atmosphere through valve element 50, with the proviso that the positive pressure thus created is greater than the opening pressure of valve element 50, i.e. greater than the pressure provided by derivation line 49.

Similarly, during a decompression or release phase following a TC, i.e. during the release phase between two successive TCs, once the rescuer stops exerting a manual pressure on the patient's chest, the pressure in the patient's airways suddenly decreases to potentially sub-atmospheric pressures. As a consequence, the flow of oxygen coming from oxygen line 21 and travelling in first conduct element 56, is directed to the patient P to offset the pressure decrease, thereby opening the second one-way valve 55 and the first one-way valve 53, and allowing the gas flow to circulate through flexible bag 54 and tubing elements 47, 51 to the interface 6.

In addition, the pressure across valve element 50 equals to about 0 and as a result the valve element 50 is closed.

Gas insufflations regularly follow TCs and decompressions. During an insufflation, the first rescuer squeezes the bag 54 thereby closing the second one-way valve 55 that is arranged in the first conduct element 56, upstream of the flexible bag 54.

As a consequence, the flow of oxygen provided by oxygen line 21 and travelling in first conduct element 56, is directed to either a storage reservoir 59 that is fluidly connected to first conduct element 56, or vented to the atmosphere via the first exhaust valve 58 arranged on the first conduct element 56 between the storage reservoir 59 and the flexible bag 54, especially when said storage reservoir 59 is full of gas.

Gas flows out of bag 54, via a main conduct 5 comprising the first tubing element or portion 47, thereby opening the main one-way valve 53 and further traveling into derivation conduct 49. The pressure across valve element 50 equals to about 0 and, as a result, valve element 50 is closed. The gas is then directed to the patient P via the second conduct 51 element forming the downstream portion of main conduct 5, and delivered by interface 6.

After insufflation, starts an exsufflation phase, during which the first rescuer releases the flexible bag 54 that enters in expansion phase thereby sucking gas and returning to its natural state, i.e. non-squeeze state.

During said exsufflation phase, the flow of oxygen coming from oxygen line 21 and travelling in first conduct element 56, is directed towards flexible bag 54, thereby opening the second one-way valve 55. In the meantime, the patient exhales at positive atmospheric pressure which closes the main one-way valve 53 and generates a positive gradient across valve element 50, said gradient being greater than the opening pressure of said valve element 50. Consequently, gas exhaled by patient P and recovered into interface 6, further travels successively in second and third tubing elements 51, 52, before being vented to the atmosphere by valve element 50. Actually, the sudden release of flexible bag 54 quickly depressurizes chamber 50f of valve element 50 through derivation conduct 49 that is fluidly connected to chamber 50f of valve element 50.

Such a resuscitation bag system 1 is efficient but, as above explained, it provides a limited autonomy, i.e. it can be used only for a limited duration, typically less than 30 min, due to the oxygen flow rate, i.e. 15 L/min, that is delivered by such a system 1, which is often not sufficient when knowing that a cardiac massage can last up to 1 hour, or even more.

For improving the gas consumption, i.e. the amount of oxygen-containing gas delivered by the oxygen source 2 at a constant flow rate, while ensuring an insufflation of an oxygen containing gas, especially a 100% oxygen gas (i.e. pure oxygen), the resuscitation bag system 1 of FIG. 1 has been modified as explained below.

An embodiment of an improved resuscitation bag system 1 according to the present invention is shown in FIGS. 2-10. It is identical to the resuscitation bag system of FIG. 1, except that it comprises additional features, as detailed hereafter, especially a gas control unit 90, but also a recirculation unit 60 and a monitoring module 70.

Generally speaking, identical or similar elements, components and/or parts present in FIG. 1 and in FIGS. 2-10 are designated by the same reference numbers.

Similarly to FIG. 1, the resuscitation bag system 1 according to the embodiment of FIGS. 2 and 7-10, is fed by an oxygen source 2. The oxygen source 2 can be a gas cylinder 20, a gas cartridge or the like, containing for instance about 300 mL of medical-grade oxygen at 200 bars abs, which provides up to 60 L of oxygen. The oxygen source 20 comprises a low-pressure regulator 22 for reducing the $O_2$ pressure to about 100 mbar abs.

The resuscitation bag system 1 according to the present invention further comprises a monitoring module 70 as shown in FIGS. 2, 3 and 7-10, that cooperates with valve element 50.

Said monitoring module 70 comprises a module enclosure 710 that is fixed to the valve enclosure 510 of valve element 50 that is arranged in main conduct 5, i.e. downstream of the main one-way valve 53.

Monitoring module 70 comprises processing means 701, 702, also called processing unit or device, such as an electronic board 701 comprising a control unit 702 for processing data, signals or the like, such as a microprocessor, preferably a microcontroller or the like, a power source 703 for providing electrical power, such as a coin cell battery, a light emitter 705 such as a light emitting diode, and a light receiver 706, such as an avalanche photodiode. The electronic board 701 is secured to the module enclosure 710. It ensures electronic connections between the different components 702, 703, 705, 706 of the monitoring module 70 for electrically powering them and further for allowing data transmissions from receiver 706 to control unit 702.

Figure 3:
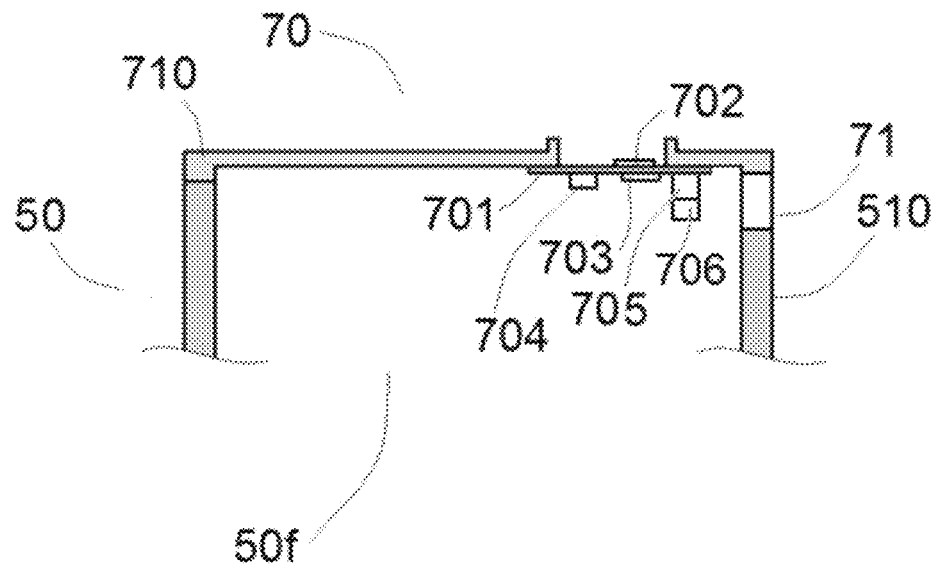
FIG. 3 shows an embodiment of a monitoring module of a resuscitation bag system according to the present invention.

In the embodiment shown in FIG. 3, the light emitter/receiver 705, 706 is facing a transparent window 71 that is arranged in the wall of the module enclosure 710. For instance, window 71 comprises a polymer or glass plate or the like, such as a polycarbonate (PC), that allows a transmission of visible light. The roles of light emitter/receiver 705, 706 and window 71 are below explained.

The power source 703 and the control unit 702 of the monitoring module 70 can 1Q also respectively provide power and further control other components of the resuscitation system 1, such as the first and second valves 92, 93 of the gas control unit 90, for instance 3:2 valves, that are connected to the monitoring module 70 via electrical connections or the like (not shown).

Figure 2:
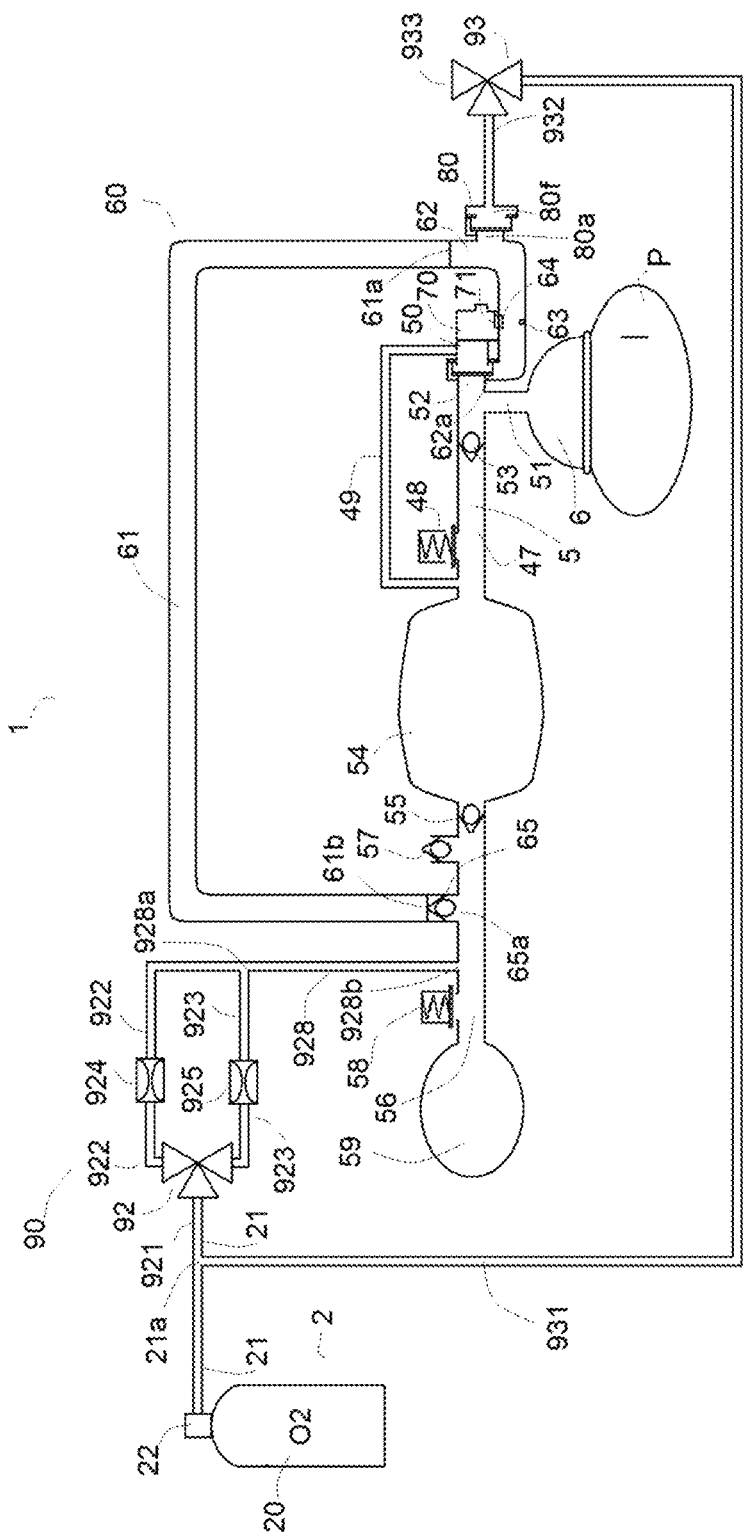
FIG. 2 shows an embodiment of an improved resuscitation bag system according to the present invention.
Figure 4:
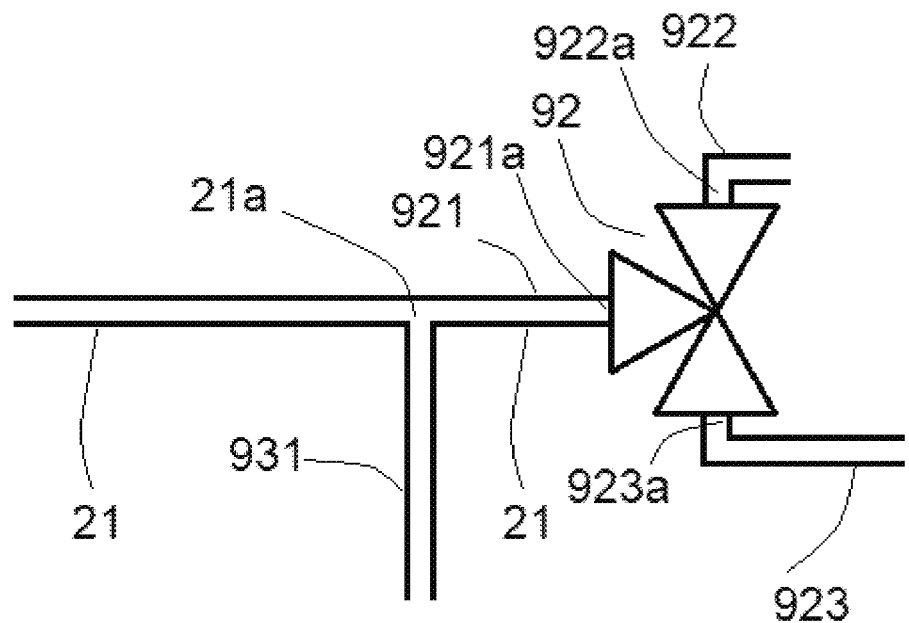
FIG. 4 shows an embodiment of a gas control unit of a resuscitation bag system according to the present invention.

Further, according to the present invention, the resuscitation bag system 1 also comprises a gas control unit 90, as shown in FIGS. 2 and 4, that is also called a gas control system, gas control means, a gas control device or the like.

Gas control unit 90 comprises a first valve 92 fluidly connected to, on the one hand, the oxygen line 21 and, on the other end, to a first 922 and second conduct 923, that are arranged in parallel, and a common line 928 fluidly connected to the first conduct element 56 of the resuscitation bag system 1.

First 922 and second conduct 923 are fluidly connected to said common line 928 so that gas traveling in either first or second conduct 922, 923, is recovered by said common line 928, conveyed in its lumen and then provided to the first conduct element 56 of the resuscitation bag system 1. In other words, the first and second conducts 922, 923 merge into the common line 928.

As shown in FIG. 4, first valve 92 comprises 3 ports comprising an entry port 921*a* fluidly connected to oxygen line 21, and a first 922*a* and second 923*a* delivery ports fluidly connected to the first 922 and second 923 conducts, respectively. Entry port 921*a* is fed with oxygen gas provided by oxygen line 21.

In operation, monitoring module 70 controls the first valve 92 for fluidly connecting entry port 921*a* to either the first or the second delivery ports 922*a*, 923*a*. When such a fluid connection is established, oxygen line 21 is fluidly connected to the first conduct 922, i.e. oxygen gas can travel into first conduct 922, whereas second conduct 923 is isolated, i.e. no fluidic connection exists, or vice versa.

First conduct 922 comprises first flow restriction means 924, i.e. a first flow restriction device, such as a first calibrated orifice or the like, through which the flow of oxygen can pass. First flow restriction means 924 constitute a first flow restriction or limitation that limits the gas flow to a first flow rate, i.e. a high flow rate value, for instance of about 15 L/min, that can depend on the pressure set by the pressure regulator 22.

Similarly, second conduct 923 comprises second flow restriction means 925, i.e. a second flow restriction device, such as a second calibrated orifice or the like, that constitute a second flow restriction or limitation limiting the gas flow to a second flow rate, i.e. a low flow rate value, for instance of about 0.5 L/min, that can also depend on the pressure set by pressure regulator 22. The second threshold value is always lower than the first threshold value.

First and second flow restriction means 924, 925 allow controlling the flow of oxygen provided by oxygen line 21 thereby obtaining two different flow rates of oxygen, for instance a first flow rate of 15 L/min and a second flow rate of 0.5 L/min, that can be provided to the common line 928 and then fed to the first conduct element 56 of the resuscitation bag system 1 according to the present invention.

Furthermore, it is also provided a bypass line 931, i.e. a gas conduct or the like, that is fluidly branched to oxygen line 21 (at 21*a*) and to an entry port 931*a* of a second valve 93 for providing oxygen thereto, as explained below and shown in FIGS. 2 and 5.

Control unit 702 of monitoring module 70 controls the second valve 93 for fluidly connecting entry port 931*a* of second valve 93 to either its first 932*a* or second 933*a* delivery ports.

Figure 5:
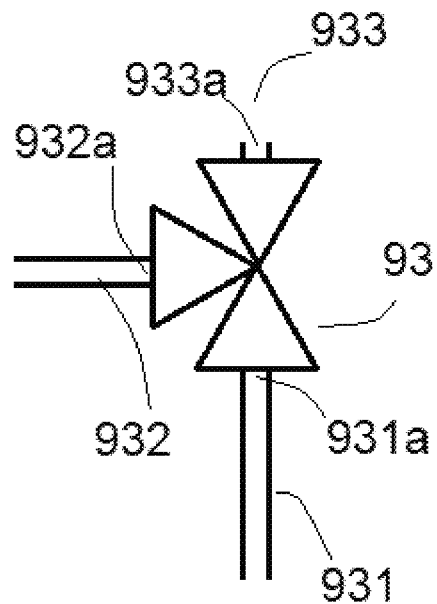
FIG. 5 shows an embodiment of a gas control unit of a resuscitation bag system according to the present invention.
Figure 6:
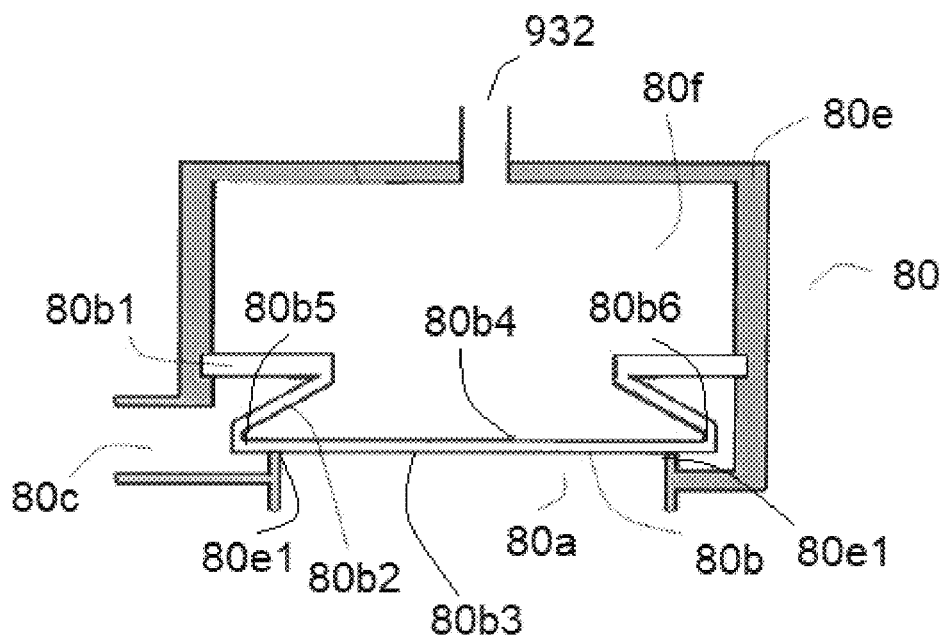
FIG. 6 shows an embodiment of a pneumatic control valve of a resuscitation bag system according to the present invention.

First 932*a* delivery port is fluidly connected to a valve conduct 932 that provides gas to the inner compartment 80*f* of an exhaust valve 80 as explained below, whereas second delivery port 933*a* is fluidly connected to the atmosphere 933 as shown in FIG. 5. Exhaust valve 80 is shown in FIG. 6.

When control unit 702 controls second valve 93 so that a fluid connection is established between the first port 931*a* and the second port 932*a*, bypass line 931 is then in fluid communication with conduct 932 so as to provide oxygen gas to said conduct 932, whereas no fluid connection exists with second port 933*a*, i.e. no gas is vented to the atmosphere 933, and vice versa.

Furthermore, the resuscitation bag system 1 of the present invention also comprises a recirculation unit 60 comprising a sensing chamber 62 or the like, fluidly connected to the exhaust port or venting port 62*a* of valve element 50 so that gas exhaled by patient P and vented by venting port 62*a* of valve element 50 is directed into sensing chamber 62.

Sensing chamber 62 further comprises an exhaust valve 80 and is fluidly connected to a $CO_2$ removal line 61 as below explained.

Sensing chamber 62 also cooperates with monitoring module 70, especially with the light emitter/receiver 705, 706 of monitoring module 70. Sensing chamber 62 comprises a sensing element 63, such as a fluorescent dye comprising a metal complex, such as a porphyrin complex for example, which is sensitive to the presence of oxygen. Sensing element 63 constitutes an oxygen sensor.

Upon excitation by the light emitter 705 of the monitoring module 70, sensing element 63 emits light at a given wavelength. The lifetime variation decay of the light emission depends on the oxygen concentration in the sensing chamber 62.

In other words, sensing element 63 responds to the presence of oxygen in the 0-100% range by fluorescence quenching. The light receiver 706 of the monitoring module 70 is configured for sensing the emission of sensing element 63 and then feeding the processing unit 702 to determine the concentration of $O_2$ into sensing chamber 62.

Sensing chamber 62 comprises another transparent window 64, which is similar to and aligned with the transparent window 71 of the monitoring module 70, so that visible light can pass through it.

This allows a remote determination of the oxygen concentration without any contact between the light emitter 705 and receiver 706, and the gas transiting into sensing chamber 62. Further, as the nature of the emission of sensing element 63 is only related to the oxygen concentration, the determination of the oxygen concentration can be performed within milliseconds.

The $O_2$ sensor, namely the sensing element 63, allows for indirectly determining that the amount of nitrogen in the lungs of the patient as the nitrogen depends on the oxygen amount, i.e. the greater the $O_2$ amount, the lower the N2 amount, and vice versa. Thus, an elevated amount of nitrogen is usually determined at the start of the treatment or when a gas leak exists, especially at the mask.

Knowing the $O_2$ amount in the gas allows for further controlling the exhaust valve 80.

As shown in FIGS. 2 and 6, sensing chamber 62 of recirculation unit 60 is further fluidly connected to the inlet conduct 80*a* of exhaust valve 80.

As shown in FIG. 6, exhaust valve 80 comprises a deformable membrane 80*b* that is tightly attached by a lip 80*b*1 to one or several grooves arranged in housing 80*e*, i.e. a rigid structure, of exhaust valve 80. A deformable portion 80*b*2 of membrane 80*b* helps membrane 80*b* to move forward or backward.

At rest, membrane 80*b* prohibits any fluid connections between inlet conduct 80*a* and an outlet conduct 80*c* of exhaust valve 80. Indeed, membrane 80*b* lays on a free edge 80*e*1 of inlet conduct 80*a*, thereby occluding said inlet conduct 80*a*. Further, a surface area difference exists between the inner 80*b*4 and the outer 80*b*3 sides of membrane 80*b*, as illustrated in FIG. 6.

The inner side 80b4 of membrane 80b is delimited by end points 80b5, 80b6, whereas its outer side 80b3 is defined as the diameter of inlet conduct 80a, delimited by edge 80e1. The surface of inner side 80b4 is hence greater than the surface of outer side 80b3 of membrane 80b.

Considering equal pressure on both sides of membrane 80b, a positive gradient force from inner side 80b4 toward outer side 80b3 is thus created. The mechanical strength of membrane 80b laying on edge 80e1 and the positive gradient force generated by the surface difference between inner side 80b4 and outer side 80b3 of membrane 80b define an opening pressure threshold in inlet 80a which moves the membrane 80b backward to allow a fluidic connection between inlet 80a and outlet 80c, as shown in FIG. 6. Depending on the size and characteristics of membrane 80b, an opening pressure as low as 5 mm $H_2O$ can be set.

Exhaust valve 80 further comprises an inner compartment 80f which is fluidly connected to valve conduct 932 as already mentioned. When valve conduct 932 provides a positive pressure to the inner compartment 80f, i.e. oxygen under pressure (e.g. at a pressure of about 100 mbar) provided by bypass line 931 and second valve 93, said positive pressure adds a pneumatic force to the opening pressure defined above, which renders the fluidic connection between inlet 80a and outlet 80c of exhaust valve 80 harder to open, unless the pressure at inlet 80a follows the increase of pressure in chamber 80f, offsetting its effect.

Exhaust valve 80 allows recirculating gas or venting it to the atmosphere depending on the amount of oxygen contained therein.

Thus, if the amount of oxygen in the gas expired by the patient P and provided to the sensing chamber 62, via the venting port 62a of valve element 50, is too low, i.e. the amount of nitrogen is too high (i.e. $N_2$-rich gas), for instance less than 90 vol. % of $O_2$, then said expired gas is vented to the atmosphere and further fresh oxygen gas is allowed to enter into the resuscitation bag system 1 of the present invention at a high flow rate, e.g. at 15 L/min, via the first gas conduct 922 comprising the first flow restriction means 924 and the common line 928a of the gas control unit 90. This allows flushing $N_2$-rich gas to the atmosphere and ensuring a concentration of oxygen of about 100% in the gas circuit and provided to the patient P. This is the case when the metabolism of the patient P is high/good, namely when the lungs of the patient ensure good gas exchanges between $O_2$ and $CO_2$.

Conversely, if the amount of oxygen in the gas expired by the patient P and provided to the sensing chamber 62 is high enough, for instance of at least 90 vol %, then the gas can be purified (i.e. $CO_2$ removal) and recirculated through a recirculation unit 60 as detailed below. In this case, it is not necessary to provide a high flow rate of oxygen as the metabolism of the patient is weak/low. Fresh oxygen is hence allowed to enter into the resuscitation bag system 1 of the present invention at a low flow rate, e.g. at 0.5 L/min, via the second gas conduct 923 comprising the second flow restriction means 925 and the common line 928a of the gas control unit 90. Such a low flow rate of oxygen is enough for ensuring a high concentration of oxygen in the gas circuit and provided to the patient P.

The recirculation unit 60 used for purifying and for recirculating oxygen-containing gas expired by the patient P comprises a CO2 removal line 61, i.e. a conduct or the like.

$CO_2$ removal line 61 comprises an upstream end 61a fluidly connected to sensing chamber 62 and a downstream end 61b fluidly connected to the first conduct element 56, as shown in FIGS. 2 and 7-10.

$CO_2$ removal line 61 comprises a $CO_2$ adsorbent, such as pellets of soda lime or any other suitable adsorbent material that can capture $CO_2$ molecules comprised in the gas exhaled by the patient, but does not remove $O_2$ molecules. The quantity of $CO_2$ adsorbent is chosen for ensuring at least 1 hour of therapy, for instance at least 0.5 kg of soda lime pellets. $CO_2$ removal line 61 can be partially or totally filled by $CO_2$ adsorbent material. $CO_2$ adsorbent material is preferably kept, e.g. sandwiched, into the $CO_2$ removal line 61 by a gas porous material, such as plastic sieves or paper filters, that are arranged in the vicinity of the upstream and downstream ends 61a, 61 b of the $CO_2$ removal line 61. Suitable soda lime products useable as $CO_2$ adsorbent material are for instance commercialized under the name Lytholyme by Allied Healthcare.

At the downstream end 61b of the $CO_2$ removal line 61, the $CO_2$-depleted gas, i.e. $O_2$-rich gas, flows through another one-way valve 65 arranged into $CO_2$ removal line 61, enters into first conduct element 56, via the outlet 65a of $CO_2$ removal line 61, where it is mixed with fresh oxygen gas provided by common line 928. The resulting $O_2$ gas flow is then conveyed by main conduct 5, namely by first and second tubing elements 47, 51, until reaching the patient P that can re-inhale it during a next inhalation phase.

Purifying and recycling the gas and controlling the oxygen flow rate allow reducing the overall oxygen consumption of the resuscitation bad system 1 of the present invention.

FIGS. 7 to 10 show how the resuscitation bag 1 of the present invention works.

Figure 7:
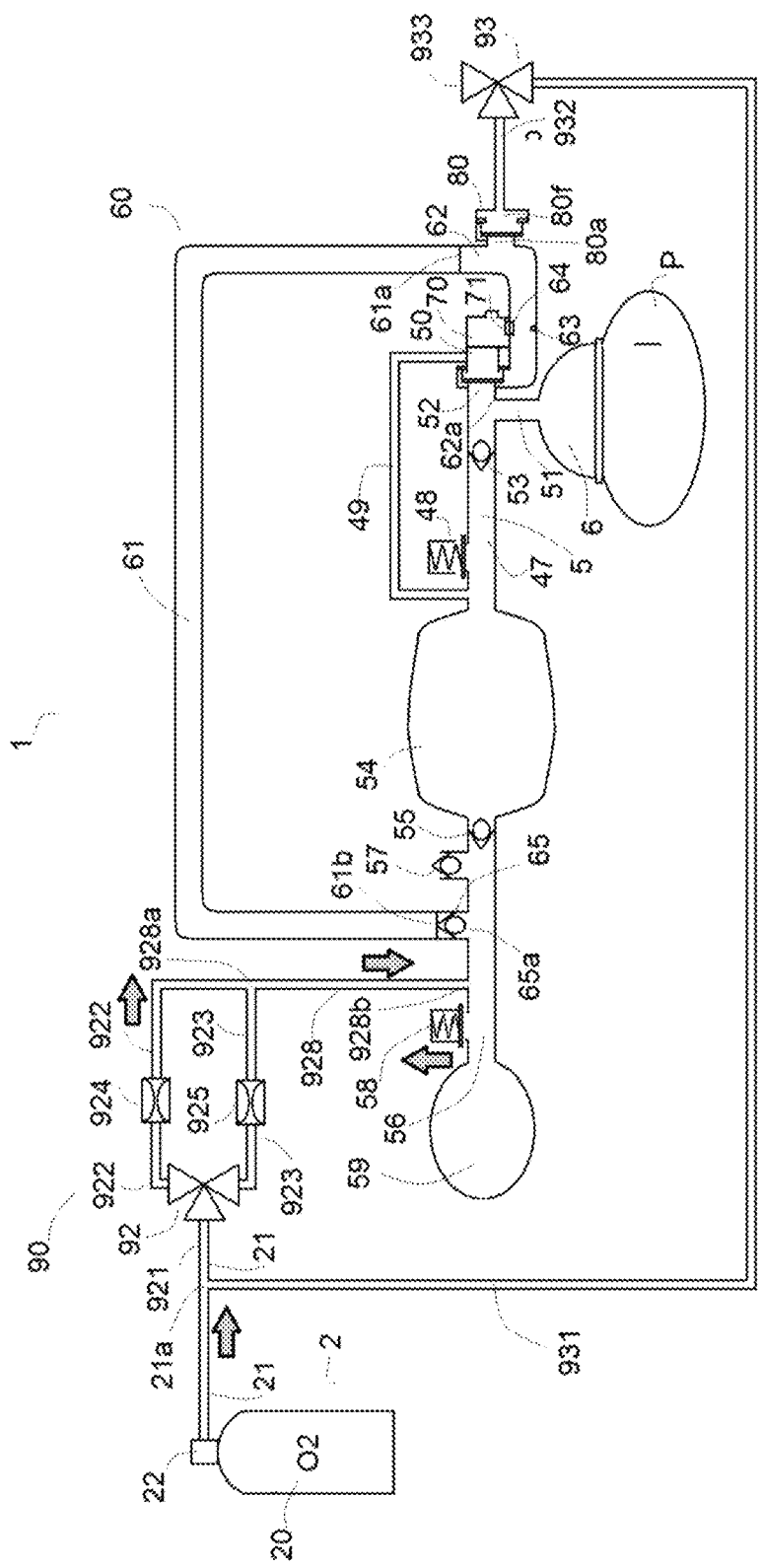
FIG. 7 illustrates how the resuscitation bag system of FIG. 2 works.

In FIG. 7, the resuscitation bag 1 is in its initial configuration. The control unit 702 of the monitoring module 70 controls:
the first valve 92 so that oxygen gas provided by oxygen line 21 can circulates into the first conduct 922, at a first flow rate, for instance 15 L/min, and
the second valve 93 so that valve conduct 932 is fluidly connected to the atmosphere 933 via the second delivery port 933a.

The oxygen flow provided by first conduct 922 enters into common line 928 and then into first conduct element 56 of the resuscitation bag 1.

Flexible bag 54 is in its initial configuration, e.g. in a "steady" state. Flexible bag 54 and storage reservoir 59 are filled with oxygen.

As the pressure differential across valve element 50 equals about 0, valve element 50 is closed so that no gas can pass from tubing element 52 to sensing chamber 62.

Any oxygen in excess in first conduct element 56, i.e. any over-pressure, is vented to the atmosphere via the first exhaust valve 58 arranged in the first conduct element 56.

Further, as valve conduct 932 of the second valve 93 is fluidly connected to the atmosphere 933, the atmospheric pressure is equally distributed into valve conduct 932 and inner chamber 80f of the exhaust valve 80. As a consequence, exhaust valve 80 exhibits a minimum opening pressure, e.g. any pressure greater than 5 mm $H_2O$ in sensing portion 62 would open exhaust valve 80 and vent the gas to the atmosphere.

Figure 8:
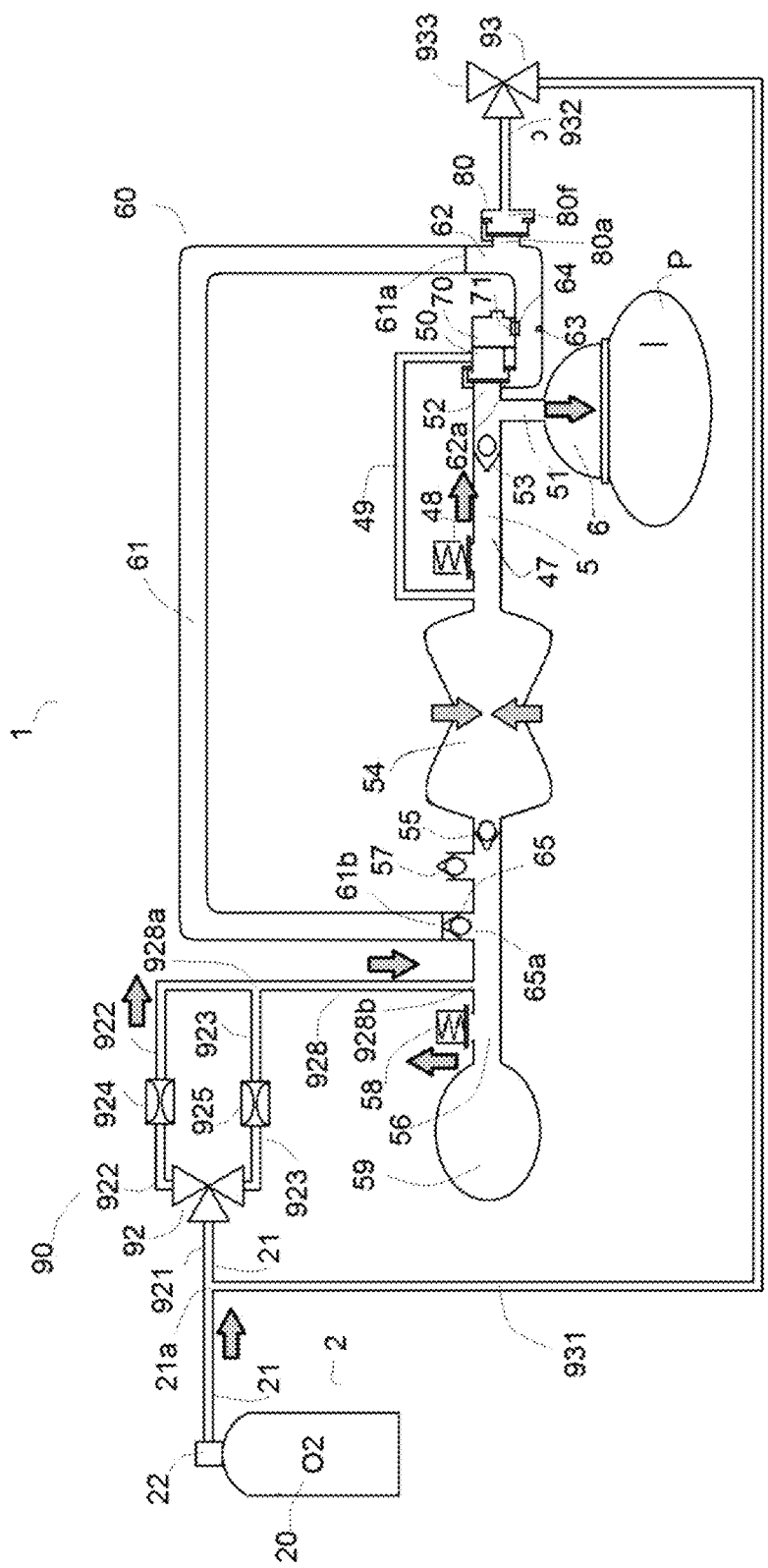
FIG. 8 illustrates how the resuscitation bag system of FIG. 2 works.

As shown in FIG. 8, during a gas insufflation phase, a rescuer, i.e. medical staff or the like, squeezes the flexible bag 54 thereby delivering $O_2$-gas into the lumen of the main conduct 5. The gas circulates into the main conduct 5 toward the patient P. In particular, it passes through the main one-way valve 53 and also enters into derivation conduct 49. Consequently, the pressure across valve element 50 equals to about 0 mbar and valve element 50 is closed so that the gas is directed toward the patient P via the second tubing element 51, i.e. a conduct or the like, and the interface 6, namely a mask or the like.

Figure 9:
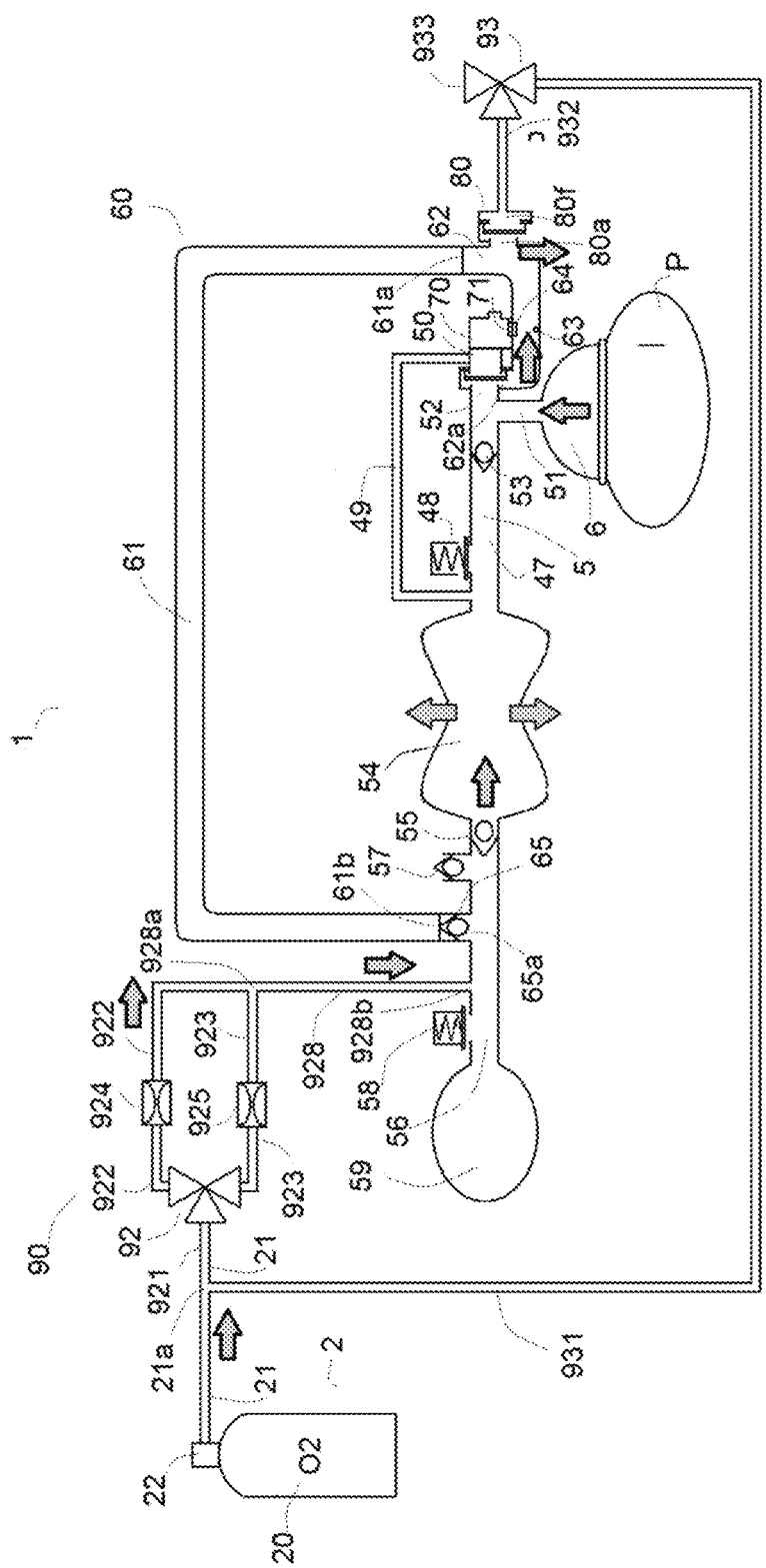
FIG. 9 illustrates how the resuscitation bag system of FIG. 2 works.

The gas insufflation phase is followed by an exsufflation phase, during which the rescuer releases the flexible bag 54 so that it enters into an expansion phase (at sub atmospheric pressure) for returning to its natural state, as shown in FIG. 9.

During this phase, the flow of oxygen provided by oxygen line 21 circulates successively into the gas control unit 90, the common conduct 928, and the first conduct element 56, through the second one-way valve 55, and then enters into flexible bag 54. The sudden release of flexible bag 54 quickly depressurizes chamber 50*f* of valve element 50 via the derivation conduct 49.

In the meantime, the patient P exhales at positive atmospheric pressure, which closes the main one-way valve 53 and generates a positive gradient across valve element 50, said gradient being greater than the opening pressure of said valve element 50. Consequently, the gas exhaled by the patient P can enter into the sensing chamber 62, via the second and third tubing elements 51, 52, and the exhaust port 62*a* of the valve element 50.

As valve conduct 932 of the second valve 93 is still fluidly connected to atmosphere 933, exhaust valve 80 opens as soon as the pressure in sensing chamber 62 exceeds its opening pressure, namely about 5 mm $H_2O$. Consequently, all the gas exhaled by patient P is vented to the atmosphere as inlet 80*a* and outlet 80*c* of exhaust valve 80 are fluidly connected.

During this exsufflation phase, the gas exhaled by the patient contacts the sensing element 63 in the sensing chamber 62. Multiple excitations by light emitter 705 are reflected by sensing element 63 and sensed back by receiver 706 so that a real time profile of the oxygen concentration in sensing chamber 62 can be established by the control unit 702.

As the exsufflation phase takes place at the onset of the therapy, the lungs of patient are mainly filled with nitrogen present in ambient air (i.e. about 80% of $N_2$), Consequently, the real time profile of the oxygen concentration in sensing chamber 62 decreases from about 100% at the beginning of the exsufflation phase (i.e. oxygen from the previous insufflation and present in the upper airways) to a minimum value representing how much nitrogen is remaining in the lungs of the patient. This minimum value, determined by control unit 702, defines a future configuration of the system for the upcoming thoracic compressions. Thus, if the minimum oxygen concentration measured during the exsufflation phase is lower than a set threshold, for instance 90%, control unit 702 can determine that nitrogen in the lungs of the patient has not been completely flushed away and therefore keeps the initial configuration of the first and second valves 92, 93 and therefore fluid connections between oxygen line 921 and first conduct 922, on the one hand, and valve conduct 932 and atmosphere 933, on the other hand.

While TCs can play a role in the initial denitrogenation of the lungs, most of the clearance is performed by repeated insufflations, Knowing that a complete N2 clearance is done within about 10 breaths and further that about 10 insufflations are performed within 1 min, the lungs of a patient are cleared of $N_2$ and filled with about 100% $O_2$ after 1 minute of insufflations and TCs, e.g. which corresponds to about 15 L of $O_2$ from oxygen source 2.

Thus, after about 1 minute after the care has started, the real time profile of the oxygen concentration in sensing chamber 62, determined by control unit 702, equals the threshold set by said control unit 702, for instance 90 vol. %, meaning that the denitrogenation phase of the lung is done.

In an economy mode configuration, wherein the oxygen concentration in sensing chamber 62 is above said threshold (>90 vol. %), control unit 702 controls the first valve 92 so that conducts oxygen line 21 and second conduct 923 are fluidly connected, and the second valve 93 so that bypass line 931 and valve conduct 932 are also fluidly connected and the $O_2$ flow is limited to 0.5 L/min.

The flow oxygen enters into the first element conduct 56 and then fills the flexible bag 54 and/or the reservoir 59 if needed, or is vented to the atmosphere by first exhaust valve 58. Further, the gas pressure downstream of pressure regulator 22, e.g. 100 mbar abs, is distributed successively into oxygen line 21, bypass line 931 and valve conduct 932, and then said pressure applies on membrane 80*b* of exhaust valve 80, prohibiting any fluid connection between inlet conduct 80*a* and the ambient atmosphere, i.e. any venting to the atmosphere.

The subsequent insufflation phase is the same as described above. However, the new exsufflation phase following this subsequent insufflation phase differs from the one shown in FIG. 9.

Figure 10:
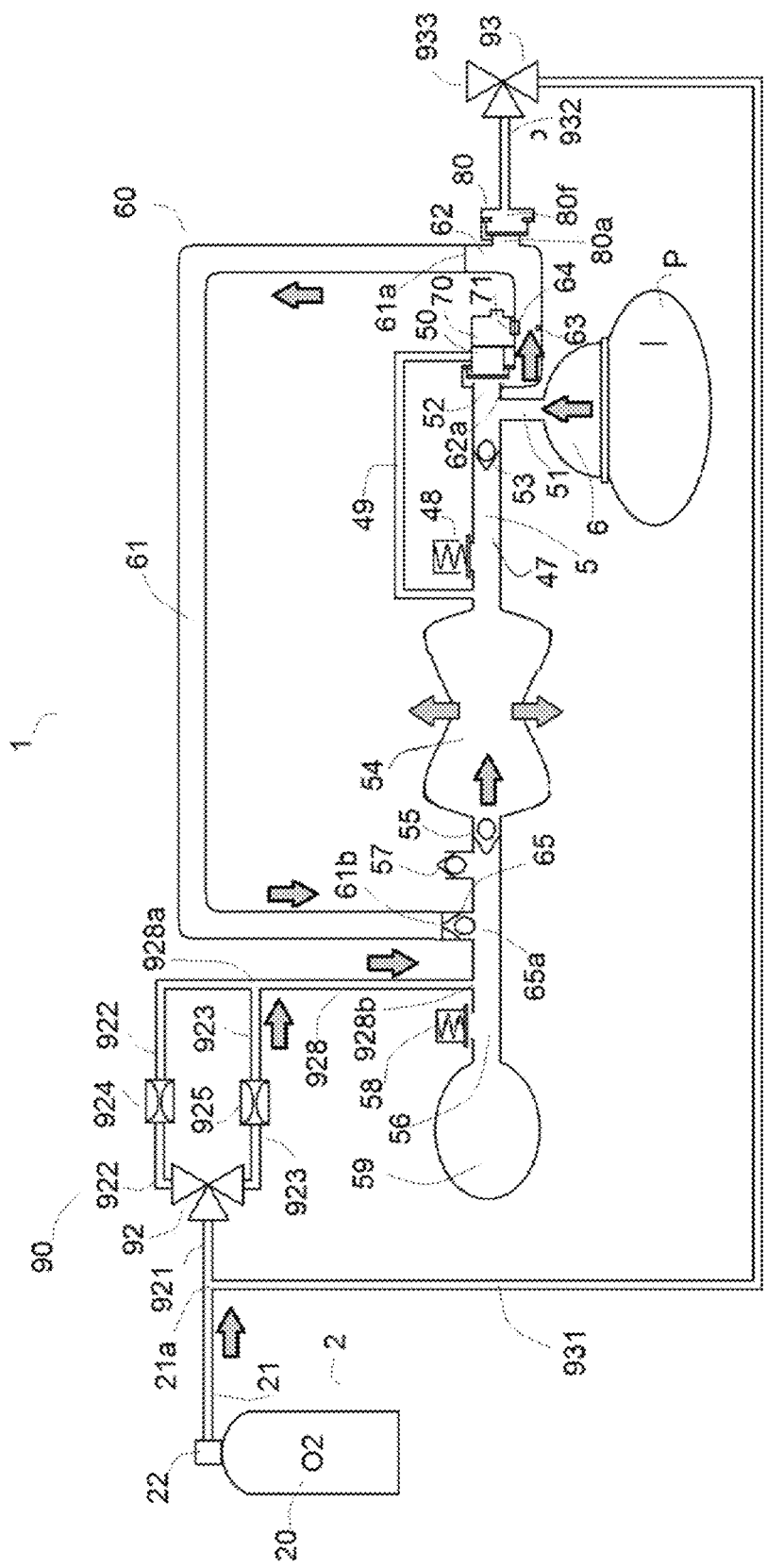
FIG. 10 illustrates how the resuscitation bag system of FIG. 2 works.

Indeed, during said new exsufflation phase, as shown in FIG. 10, the flow of oxygen coming from common conduct 928 (i.e. 0.5 L/min) enters into the first conduct element 56 and is then directed towards the flexible bag 54. In the meantime, the patient exhales at positive atmospheric pressure, which closes the main one-way valve 53 and generates a positive gradient across valve element 50, said gradient being greater than the opening pressure of said valve element 50.

Consequently, gas exhaled by patient P travels successively in the second and third tubing elements 51, 52, and reaches sensing chamber 62 via the exhaust port 62*a* of valve element 50.

As the pressure existing into sensing chamber 62 is lower than the pressure in chamber 80*f* of exhaust valve 80, which remains closed, all the gas exhaled by patient P further travels into the recirculation unit 60, especially removal portion 61, where potential traces of $CO_2$ are removed.

Ultimately, the gas volume exhaled by patient P during the TCs opens the one-way valve 65 and enters into first element conduct 56 (at 65*a*) where it mixes with the oxygen flow coming from common conduct 928 thereby helping re-inflating the flexible bag 54.

Subsequent Tcs occurring after this exsufflation phase have the same effect on the different components of resuscitation bag system 1, except that during the TC phase, the gas passing through valve element 50 further travels into the recirculation unit 60 to get rid of potential $CO_2$ and re-enters into the first element conduct 56 (at 65*a*) as fresh gas.

Thanks to the resuscitation bag system 1 of the present invention, the minimum oxygen flow coming from the oxygen source 2, namely 0.5 L/min, is greater than either the oxygenation uptake of the patient and/or the maximum $CO_2$ exhaled by said patient 1, that is removed by the removal portion 61. Considering a first "priming" stage requiring about 15 L over the first minute, and subsequently 0.5 L/min to sustain the metabolism of the patient, a container of 60 L allows a patient resuscitation for about 90 mn, as opposed to 4 mn at a continuous flow of 15 L/min.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A resuscitation bag system (1) useable for resuscitating a person in cardiac arrest, comprising:
   a hollow flexible bag (54) comprising an inlet (54*a*) and an outlet (54*b*),
   a first conduit element (56) fluidly connected to the inlet (54*a*) of the hollow flexible bag (54) for providing gas to said flexible bag (54), and
   a main conduit (5) fluidly connected to the outlet (54*b*) of the hollow flexible bag (54) for conveying gas provided by said flexible bag (54), and
   a gas control unit (90) comprising a first valve (92) fluidly connected to a first (922) and to a second conduit (923), said first (922) and second conduits (923) being arranged in parallel and further fluidly connected to the first conduit element (56), the first conduit (922) comprising a first flow restrictor (924) configured for limiting the gas flow to a first flowrate, and the second conduit (923) comprising a second flow restrictor (925) configured for limiting the gas flow to a second flowrate, said second flowrate being less than the first flowrate.

2. The resuscitation bag system (1) of claim 1, wherein the first valve (92) of the gas control unit (90) is controlled by a monitoring module (70) adapted to direct the gas into the first conduit (922) or the second conduit (923).

3. The resuscitation bag system (1) of claim 1, wherein the first and second conduits (922, 923) are fluidly connected to the first conduit element (56) by a common line (928).

4. The resuscitation bag system (1) of claim 1, wherein the first flow restrictor (924) comprises a first calibrated orifice for limiting the gas flow to the first flowrate.

5. The resuscitation bag system (1) of claim 1, wherein the second flow restrictor (925) comprises a second calibrated orifice for limiting the gas flow to the second flowrate.

6. The resuscitation bag system (1) of claim 2, wherein the monitoring module (70) comprises an electronic board (701) comprising a control unit (702) for processing data (701, 702).

7. The resuscitation bag system (1) of claim 2, wherein the monitoring module (70) further comprises a light emitter/receiver (705, 706).

8. The resuscitation bag system (1) of claim 2, further comprising:
   a valve element (50) arranged in the main conduit (5) and comprising a venting port (62*a*), and
   a main one-way valve (53) arranged in the main conduit (5), between the hollow flexible bag (54) and the valve element (50).

9. The resuscitation bag system (1) of claim 8, further comprising a derivation line (49) fluidly connected to the main conduit (5), between the hollow flexible bag (54) and the main one-way valve (53), and further to the valve element (50), the derivation line (49) adapted for controlling the opening or closing of said valve element (50).

10. The resuscitation bag system (1) of claim 4, wherein the first calibrated orifice is configured for limiting the gas flow to the first flowrate of greater than 10 L/min.

11. The resuscitation bag system (1) of claim 5, wherein the second calibrated orifice is configured for limiting the gas flow to the second flowrate of less than 2 L/min.

12. The resuscitation bag system (1) of claim 8, wherein the monitoring module (70) is fixed to the valve element (50).

13. The resuscitation bag system (1) of claim 6, wherein the control unit (702) comprises a microcontroller.

14. A gas delivery assembly (1, 2) comprising:
   the resuscitation bag system (1) according to claim 8, and
   a source of oxygen (2) fluidly connected to the first valve (92) of the resuscitation bag system (1) via an oxygen line (21).

* * * * *